United States Patent [19]

Piccolini et al.

[11] Patent Number: 4,490,476

[45] Date of Patent: Dec. 25, 1984

[54] CATALYST FOR THE PREPARATION OF $\alpha,\beta$-UNSATURATED COMPOUNDS

[75] Inventors: Richard J. Piccolini, Newtown; Michael J. Smith, Southampton, both of Pa.

[73] Assignee: Rohm and Haas Company, Philadelphia, Pa.

[21] Appl. No.: 508,624

[22] Filed: Jun. 28, 1983

[51] Int. Cl.³ ..................... B01J 21/02; B01J 27/14
[52] U.S. Cl. ..................................... 502/203; 502/208
[58] Field of Search ............... 252/428, 430, 432, 435, 252/437; 502/203, 208

[56] References Cited

U.S. PATENT DOCUMENTS

| | | | |
|---|---|---|---|
| 2,210,148 | 8/1940 | Indest | 252/435 |
| 2,339,247 | 1/1944 | Danforth | 252/432 X |
| 2,339,249 | 1/1944 | Danforth | 252/432 X |
| 2,341,363 | 2/1944 | Connolly | 252/432 X |
| 2,392,588 | 1/1946 | Greensfelder et al. | 252/432 X |
| 2,422,884 | 6/1947 | Burgin | 252/432 X |
| 2,480,672 | 8/1949 | Plank | 252/432 |
| 2,564,268 | 8/1951 | Mathy et al. | 252/432 X |
| 2,652,434 | 9/1953 | Johnstone | 252/432 X |
| 3,014,958 | 12/1961 | Koch et al. | 260/486 |
| 3,840,587 | 9/1974 | Pearson | 260/486 D |
| 3,933,888 | 1/1976 | Schlaefer | 260/465.9 |
| 3,950,478 | 4/1976 | Kenworthy et al. | 252/464 |
| 4,085,143 | 4/1978 | Holmes | 260/515 R |
| 4,118,588 | 10/1978 | Fouquet et al. | 560/210 |
| 4,147,718 | 4/1979 | Gaenzler et al. | 260/465.9 |
| 4,165,438 | 8/1979 | Schneider | 560/211 |
| 4,392,984 | 7/1983 | Engelbach et al. | 252/432 |

OTHER PUBLICATIONS

Ninth Edition Merck Index, p. 49, entry 358.
Vitcha et al., *Vapor Phase Aldol Reaction*, "I&EC Product Research and Development," vol. 5, No. 1, (Mar. 1966), pp. 50–53.

*Primary Examiner*—Delbert E. Gantz
*Assistant Examiner*—William G. Wright
*Attorney, Agent, or Firm*—Terence P. Strobaugh

[57] ABSTRACT

A new catalyst for preparing $\alpha,\beta$-unsaturated compounds through vapor phase aldol condensation wherein the catalyst is a supported boron and/or phosphorous catalyst.

8 Claims, No Drawings

CATALYST FOR THE PREPARATION OF α,β-UNSATURATED COMPOUNDS

This invention is directed to novel catalysts and their use in the preparation of α,β-unsaturated compounds by vapor phase aldol condensation employing formaldehyde or a formaldehyde precursor and a saturated compound containing one less carbon atom than the unsaturated compound. The catalyst is comprised of boron or phosphorous on a support or both boron and phosphorous on a support. The boron and phosphorous are present in their oxygenated forms.

α,β-Unsaturated compounds are very useful in the preparation of resins, fibers and other polymers having a multitude of uses. Therefore, the search for more economical methods of preparation and, also, environmentally safer methods of preparation are continually being sought after.

References which disclose condensation reactions are Vitcha et al., *Vapor Phase Aldol Reaction,* "I&EC Product Research and Development," Vol. 5, No. 1, (March, 1966) at pages 50-53 wherein the vapor phase reaction of acetic acid and formaldehyde is described employing catalysts such as calcium aluminosilicate, or a sodium aluminosilicate with calcium chloride. See also U.S. Pat. Nos. 4,147,718; 4,118,588; 4,165,438; 4,085,143; 3,933,888; 3,840,587 and 3,014,958 and references cited therein.

The process for preparing an α,β-unsaturated compound of the formula: $CH_2=CRCOR^1$ comprises treating a compound of the formula: $RCH_2COR^1$ or $RCH_2CO-O-COCH_2R$ with formaldehyde or a precursor of formaldehyde in the vapor phase at a temperature generally in the range of from about 220° to about 450° C. in the presence of a catalyst to be described below.

The substituent R, above, can be hydrogen, alkyl, aralkyl or aryl of from 1-10 carbon atoms, for example, a straight or branched-chain alkyl of from 1 to 6 carbon atoms; $R^1$, above, can be hydrogen, hydroxy, lower alkyl of from 1 to 6 carbon atoms, lower alkoxy of from 1 to 6 carbon atoms, aryl such as phenyl, amino, di-lower alkyl amino, and the like. The R groups in the anhydrides can be the same or different radicals. Anhydrides which can be employed include acetic, propionic, phenylacetic, butyric, pentanoic, hexanoic anhydride or mixed anhydrides thereof.

The catalyst employed in this process is represented by the following formula:

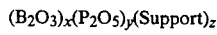

wherein x and y each have a value of 0 to 1 and the sum of x plus y is 1 and z has a value of 0.5 to 999. The x, y and z refer to parts by weight of the materials.

Catalysts are prepared by mixing some combination of boron phosphate, boric acid, phosphoric acid, nitrogeneous species, and other materials to be supported, in water. The catalyst is placed on a support. Silica gel (granular, high surface area) is preferred. The materials are kept together for from 12 to 24 hours at a temperature in the range of from about 50° to about 80° C., in a convection oven, after which the water is removed by rotary evaporation. The solid residue is dried, then cooled under a dry nitrogen sparge. This material is ready for post-treatments (for example, $BF_3$ treatment or calcining) prior to use as a catalyst.

The percentage of ($B_2O_3$) and/or ($P_2O_5$) on the support can vary from 1% to 99%; however, we have found that a preferred percentage is in the range from 3% to 30%. To illustrate further, at 3% the formula of the catalyst is $(B_2O_3)_{0.295}(P_2O_5)_{0.705}(Support)_{32.33}$. At 10% the formula is: $(B_2O_3)_{0.295}(P_2O_5)_{0.705}(Support)_9$. At 30% the formula is: $(B_2O_3)_{0.295}(P_2O_5)_{0.705}(Support)_{2.33}$ The catalyst, after drying, is then ready for use; however, we have found that calcining the catalyst improves its activity. Calcining can be carried out at a temperature in the range of from about 450° to about 610° C.

We have found that we are able to increase conversion or selectivity or both of the reaction to prepare an α,β-unsaturated compound by adding a nitrogeneous material (which is removed upon calcining) to the aqueous solution during the preparation of the catalyst (improves conversion) and/or by treating the formed catalyst with an acidity enhancer either before or after calcining (improves selectivity). Preferably, the treated catalyst is calcined prior to use.

Examples of nitrogeneous materials which can be employed are, for example urea, ammonium halides such as ammonium chloride and the like, ammonium phosphates, ammonia, hexamethylenetetramine (HMTA), guanidine, or lower ($C_1$-$C_5$) or di-lower alkyl amines. It is believed that the nitrogeneous materials improve conversion because they facilitate acidity migration or create preferred surface structure or both.

Examples of acidity enhancers include Lewis acids, especially gaseous Lewis acids, such as boron trifluoride. We have found that using a combination of a nitrogeneous material and an acidity enhancer affords the best catalyst.

While catalysts prepared without a support do have activity, the use of the support has been found to substantially improve the performance of the catalyst. Examples of supports include silica, silica gels, titanium dioxide, carbonaceous adsorbents, alumina, lanthanum oxide, cordierite, zeolites or combinations thereof.

A preferred catalyst has the formula:

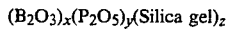

wherein x, y and z are as defined above. Silica gel is the preferred support because it affords the most active catalysts.

More preferred are catalysts which have been treated with an acidity enhancer, especially boron trifluoride. These catalysts have the formula:

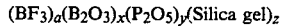

wherein x, y and z are as defined above and a is in the range of 0.1 to 1 parts by weight.

The most preferred catalyst is one which has been treated with a nitrogeneous material, especially ammonium chloride or urea and an acidity enhancer, especially, boron trifluoride. In the most preferred catalyst a is 0.49, x is 0.295, y is 0.705 and z is 9.

Reaction conditions such as contact time, temperature, amount of diluent gas and feed composition, will vary with the feed material and the particular catalyst selected. In general, the best results are obtained at a contact time of from about 0.1 to about 30 seconds. Particularly good conversions and yields are obtained using a contact time of from about 5 to about 10 seconds.

The temperature selected will be sufficient to ensure vaporization of the reactants and the products. The process may be operated at a temperature in the range of from about 190° to about 450° C. A preferred temperature range is from about 250° to about 380° C.

When acetic anhydride is employed, the preferred temperature is about 270° C. When acetic acid is employed, the preferred temperature is about 360° C.

Formaldehyde or a formaldehyde precursor such as paraformaldehyde, trioxane, tetraoxane or dimethoxymethane may be employed. Aqueous solutions of formaldehyde can also be employed.

Conversion of the formaldehyde depends on the type and state of the catalyst and, in many cases, the ratio of saturated compound to formaldehyde in the feed. Normally, the particular catalyst activity and practical manufacturing considerations will dictate the most desirable ratio of saturated precursor to formaldehyde fed to the reactor. Good results have been obtained with saturated compounds to formaldehyde ratios of from about 1.1:1 to about 8:1. The preferred ratio is from about 2.3:1 to about 5:1. The optimum ratio will depend on various considerations, such as recycling of unreacted feed materials. There appears to be no upper limit to the molar ratio other than practical manufacturing conditions which arise when a large excess of one material is introduced into a system. For example, molar ratios of 10:1 and even 20:1 could be employed.

If desired, an inert diluent gas may be utilized to facilitate feeding of the reactants, control of contact time, and the like. Good results are obtained at atmospheric pressure, using an inert diluent gas, usually in a molar ratio of gas to organic feed of from about 1:10 to about 20:1, preferably from about 1:1 to about 6:1, and most preferably about 2:1. For economical purposes an inert gas might not be used commercially. A suitable inert diluent gas is any gas which does not react with either the reactants, the products or the catalysts under the conditions of the reaction, such as nitrogen, helium, argon, or carbon dioxide.

The reactor effluent contains a mixture of the $\alpha,\beta$-unsaturated acid and unreacted starting material. The unsaturated product can be obtained by conventional distillation and can be reacted with an alcohol to form an $\alpha,\beta$-unsaturated ester.

The process of the instant invention is illustrated in greater detail by the following examples, which are all conducted at atmospheric pressure, but it will be understood that these examples are not intended to limit the invention in any way, and obvious modifications will occur to those skilled in the art.

GENERAL REACTION CONDITIONS

I. Catalyst Preparation

Catalysts are prepared by dissolution in water of some combination of boron phosphate, boric acid, phosphoric acid, ammonium halide, urea, and other materials to be supported. To this is added a support. Silica gel having a granular, high surface area of 300 m²/gm, and a pore volume of 1.0 cc/gm such as Davison Grade 57 is preferred. The materials are kept together for up to 24 hours, after which time the water is removed with agitation of the mixture to insure uniform distribution (rotary evaporation is an efficient method). The solid residue is dried for 24 hours at 70° C., then further dehydrated in a vacuum oven at 70°-110°. This material is ready for use as a catalyst.

II. Equipment Design

The catalyst is loaded into a straight glass reactor tube between 2 sections of denstone. The bed is located in the heating zone of the reactor (approximately 15" from end of tube up 7" to 23") Thermocouples are placed into the center and within an inch of the beginning of the catalyst bed. A syringe needle attached to a three-way valve is positioned into the reactor tube near its beginning (12"). Adjacent to this is another thermocouple indicating the preheat temperature. The tube is then placed vertically into a Lindberg tube furnace and brought up to temperature under a helium carrier of 80 cc/min. The carrier is split allowing one part to flush thru the needle, the other to flush the tube as make up. The flows are recorded directly from rotameters.

III. Reaction Conditions

The catalyst is first calcined at a temperature in the range of from 450° to 610° C. and usually in the range of from about 500° to 520° C. under an air flow of 125 mm/min for 16 hrs. The procedure is to bring the catalyst up to the desired temperature (500° C.) under a helium carrier of 80 cc/min and then switch carriers to air. The catalyst is then cooled to the desired temperature under helium and the run continued.

Feed syringes, collectors and $CO_2$ and $H_2O$ traps are weighed prior to each run, weights recorded and the equipment positioned into the system and the run started. Just before the run ends, the temperatures and flow rates are again recorded and the liquid feed stopped. The helium carrier is increased by ⅓ and the traps and collector left an additional ten minutes. After removal, the syringe, traps and collectors are weighed and recorded.

Samples are taken from the traps and mixed with diglyme, an internal standard, in a 7:1 weight ratio (sample to diglyme). These values are then divided by the total amount of product collected and a value obtained and used in the method for glc analysis. The samples are analyzed twice and the averages used to calculate conversions and the selectivities.

The conditions for the runs are as follows:

| | |
|---|---|
| Temperature | 360° C. |
| Carrier | helium at 80 cc/min |
| Liquid Feed Rate | RATE: 0.24 ml/min |
| Run Time: | 45 minutes |
| Catalyst Volume | 70 cc (unless specified differently) |

CATALYST PREPARATION

EXAMPLE 1

Step A: $(B_2O_3)_{0.3}(P_2O_5)_{0.7}(Silica\ gel)_{10.3}$

Boric acid (9.87 g) is placed in a 1000 ml. round bottomed flask. To this is added water (500 ml). This mixture is warmed until the boric acid dissolves. To this solution is added phosphoric acid (85%) (21.98 g) and the whole diluted to a volume of 800 ml with dionized water.

EXAMPLE 1B

Step B: $(B_2O_3)_{0.3}(P_2O_5)_{0.7}$(Silica gel)$_{10.3}$—(urea treated)

To urea (18.47 g) is added one-half the reaction mixture of Step A (400 ml). To the solution is added silica gel (98.65 g). The reaction mixture is heated at 70° C. for 16 hours and then most of the water is removed. Wgt. 162.25 gr.

EXAMPLE 1C

Step C: $(B_2O_3)_{0.3}(P_2O_5)_{0.7}$(Silica gel)$_{10.3}$—(ammonium chloride treated)

To ammonium chloride (23.39 g) is added one-half of the reaction mixture of Step A of Example 1. To the solution is added silica gel (98.705 g). The reaction mixture is heated at 70° C. for 16 hours. Most of the water is removed. Wgt. 168.0 g.

EXAMPLE 2

$(B_2O_3)_{0.26}(P_2O_5)_{0.74}$(Silica gel)$_{3.23}$

Boron oxide (4.0 g) is dissolved in hot distilled water (200 ml). To the solution is added silica gel (50 g) and the mixture is heated at 65° C. until most of the water is removed and the result appears as white granules (about 3 days). These granules are added to a solution of 100% phosphoric acid (11.5 g) and anhydrous isobutanol (100 ml). The mixture is allowed to stand 1 hour and then the supernatent liquid is decanted. The residue is washed once with isobutanol and dried at 65° C.

EXAMPLE 3

$(B_2O_3)_{0.19}(P_2O_5)_{0.81}$(Silica gel)$_{5.24}$

Boron phosphate (12.09 g) is dissolved in distilled water (750 ml) with heating (the solution turns from milky cloudy to clear) and then silica gel (110 g) is added. The water bubbled and warmed up. Phosphoric acid (0.66 g of 85%) is added immediately thereafter and the solution is swirled (it turns cloudy). The material (in a large beaker capped with filter paper) was placed in a 73° C. convection oven and swirled periodically. The oven-dried residue is transferred to a beaker and weighed (amounting to 168.0 g). This residue is dried in a vacuum oven at 60° C. After drying, the catalyst weighs 143.6 g. It is placed in a 500° C. furnace (in air) for drying and calcining to yield 116.8 g.

EXAMPLE 4

$(B_2O_3)_{0.288}(P_2O_5)_{0.712}$

Boric acid (10.0 g., 0.16 moles) and 85% phosphoric acid (22.17 g., 0.19 moles) are dissolved in water (700 ml). To this is added silica gel (200 g.). The resulting material is placed in a 60° C. oven with a foil cap overnight, after which the water is removed by rotary evaporation and the solid residue dried for 16 hrs. at 60° C. to afford 54.22 g of material. This is added to a solution of ammonium phosphate, dibasic (5.0 g.; 0.038 moles) in water (120 ml.). This mixture is placed in a 65° C. oven with a foil cap for 2 days. The water is removed by rotary evaporation, the solid residue dried for 16 hrs. at 65° C. and the preparation is ready for use as a catalyst.

By following substantially the procedures in examples 1–4 and by substituting the appropriate starting materials, other catalyst can be prepared. The following table illustrates the starting materials, the amounts of each employed, reaction time and weight of catalyst.

TABLE I

| Ex. No. | $H_3BO_3$ g | Boron Phosphate g | $H_3PO_4$ (85%) g | Nitrogeneous Species Amt. | Nitrogeneous Species Type | Silica Gel g | Water ml | Rest Time hrs | Wt. of Result* g |
|---|---|---|---|---|---|---|---|---|---|
| 5 | 0 | 6.055 | 1.215 | 0 | 0 | 50.01 | 350 | 16 | 53.25 |
| 6 | 0 | 1.557 | 0.45 | 0 | 0 | 49.95 | 340 | 24 | 48.9 calcined @ 500° C. |
| 7 | 0 | 5.0 | 0.55 | 0 | 0 | 51.9 | 225 | 1 | — |
| 8 | 0 | 1.557 | 0.30 | 0 | 0 | 50.0 | 340 | 1 | calcined @ 600° C. |
| 9 | 5.0 | 0 | 11.032 | 0 | 0 | 100.0 | 350 | 16 | — |
| 10 | 7.881 | 0 | 17.53 | 29.56 | urea | 159.11 | 600 | 96 | |
| 11 | 3.157 | 0 | 7.10 | 11.83 | HMTA | 64.05 | 300 | 16 | 107.9 |
| 12 | 0 | 3.00 | 0.588 | 0 | 0 | 34.99 | 350 | 16 | 45.247 |
| 13 | 1.753 | 0 | 3.858 | 0 | 0 | 34.99 | 250 | 16 | 46.57 |
| 14 | 1.40 | 0 | 3.089 | 0.6 | urea | 27.3 | 300 | 16 | 31.528 |
| 15 | 1.40 | 0 | 3.089 | 7.6 | $NH_4Cl$ | 27.3 | 300 | 16 | — |

*Uncalcined weight unless stated otherwise.

PREPARATION OF CATALYST TREATED WITH AN ACIDITY ENHANCER

For increased selectivity, a $BF_3$ treated catalyst may be prepared as follows: After loading into the reactor tube, which is heated to 360°, the catalyst bed (70 cc) is treated by adding a solution of $BF_3$ (1.94 g) in acetic acid (11.23 g) to the reactor tube over a 15 minute period. Afterward, it may be used as is, but preferably, is calcined prior to use. Table II gives the results of runs made on $BF_3$ treated catalysts. Conversion can be increased by pretreatment also. When urea or ammonium chloride are loaded on a B-P/silica gel catalyst and the system subsequently calcined, high formaldehyde conversions result.

EXAMPLE 16

$(BF_3)_{0.48}(B_2O_3)_{0.3}(P_2O_5)_{0.7}$(Silica gel)$_{10.3}$

The catalyst (47.18 g) of Example 1 loaded into a glass reactor tube as described under "General Reaction Conditions" and placed into a tube furnace. The reactor is heated to 360° C. under a helium flow of 80 cc/min. and then the catalyst is treated with a $BF_3$ solution. It is then calcined under an air flow of 125 cc/min for 16 hrs. at 500° C., cooled and then employed in a vapor phase run according to procedures described under "General Reaction Conditions".

EXAMPLE 17

Boron oxide (12.0 g., 0.17 moles) is dissolved in water (600 ml.) and silica gel (150 g.) is added. This material is placed in a 65° C. oven with a foil cap overnight, whereupon the water is removed by rotary evaporation and the solid residue dried.

Dry ether (150 ml.) is placed in a 500 ml. round bottom flask and 40.2 g. of the above preparation added. Commercial 1:1 boron trifluoride-phosphoric acid (12.24 g., 0.074 moles) and 100% phosphoric acid (30 g., 0.306 moles) are each dissolved in ether (60 ml.) and carefully added to the mixture. The resultant mixture is stirred overnight and the solvent removed by rotary evaporation. The solid is ready for use as a catalyst.

The catalyst is loaded into a glass reactor tube and placed vertically into a Lindberg tube furnace. The catalyst is heated to 360° C. under helium carrier and then treated with a $BF_3$-2HOAc/HOAc solution. (The amount of solution passed over the catalyst is proportional to the charge size using 5.65 g $BF_3$ 2HOAc/7.5 g HOAc for a 70 cc charge as the basis).

The catalyst is then calcined at 500° C. under air for 16 hrs. The temperature is again lowered to 360° C. and helium carrier restored. The reaction is run according to procedures described in "General Reaction Conditions".

EVALUATION OF CATALYSTS

TABLE II

| Run No. | Catalyst from | Ratio[1] | Temp. °C. | Formaldehyde | | | | Acetic Acid | |
|---|---|---|---|---|---|---|---|---|---|
| | | | | C[2] | × | S[3] | = Yield | C | S |
| 1 | Ex. 2 | 2.3 | 355 | 54.2 | × | 82.3 | = 44.6 | 23.6 | 81.4 |
| 2 | Ex. 2 | 1.31 | 355 | 33.3 | × | 88.8 | = 29.6 | 22.5 | 100 |
| 3 | Ex. 2 | 4.99 | 355 | 78.9 | × | 83.7 | = 66.0 | 20.0 | 66.0 |
| 4 | Ex. 3 | 2.3 | 358 | 57.1 | × | 87.9 | = 50.2 | 26.5 | 82.6 |
| 5 | Ex. 3 | 2.3 | 358 | 74.0 | × | 71.7 | = 53.1 | 35.8 | 64.5 |
| 6 | Ex. 5 | 2.3 | 358 | 55.7 | × | 82.9 | = 46.2 | 25.8 | 76.7 |
| 7 | Ex. 6 | 2.3 | 360 | 56.1 | × | 76.8 | = 43.1 | 29.4 | 62.8 |
| 8 | Ex. 7 | 2.3 | 375 | 56.6 | × | 82.4 | = 46.6 | 25.6 | 78.1 |
| 9 | Ex. 8 | 2.3 | 357 | 48.2 | × | 79.2 | = 38.2 | 23.0 | 71.4 |
| 10 | Ex. 9 | 2.3 | 357 | 71.8 | × | 73.3 | = 52.6 | 32.6 | 69.3 |

Calcining 500°–520° C. in air
[1] Feed Ratio of acetic acid to formaldehyde
[2] $C = \text{Conversion} = \dfrac{\text{moles of material in} - \text{moles of material out}}{\text{mole of material in}}$
[3] $S = \text{Selectivity} = \dfrac{\text{moles of unsaturated compound out}}{\text{moles of material in} - \text{moles of material out}}$ The products of examples 6, 8, 1B, 1C, 10, 11 and 15 are treated with $BF_3$ to afford examples 18, 19, 20, 21, 22, 23 and 16, respectively.

Example 14 is the product of example 9 treated with urea and example 15 is the product of example 9 treated with ammonium chloride.

TABLE III

Treated Catalyst

| Run No. | Catalyst From | Ratio | Temp. °C. | Formaldehyde | | | | Acetic Acid | |
|---|---|---|---|---|---|---|---|---|---|
| | | | | C | × | S | = Yield | C | S |
| 11 | Ex. 14 | 2.33 | 355 | 89.4 | × | 63.7 | = 56.9 | 36.1 | 67.7 |
| 12 | Ex. 14 | 8.0 | 355 | 97.2 | × | 61.1 | = 59.4 | 20.6 | 37.0 |
| 13 | Ex. 15 | 2.33 | 355 | 91.7 | × | 65.4 | = 60.0 | 36.5 | 70.7 |
| 14 | Ex. 15 | 8.0 | 355 | 98.0 | × | 62.4 | = 61.2 | 20.3 | 38.7 |
| 15 | Ex. 17 | 2.33 | 362 | 90.6 | × | 91.7 | = 82.0 | 39.2 | 90.9[a] |
| 16 | Ex. 17 | 2.33 | 360 | 72.9 | × | 91.0 | = 66.4 | 31.5 | 90.5[b] |
| 17 | Ex. 17 | 2.33 | 361 | 63.6 | × | 84.7 | = 53.9 | 29.1 | 79.6[c] |
| 18 | Ex. 18 | 2.33 | 353 | 65.5 | × | 89.3 | = 58.5 | 29.9 | 83.9 |
| 19 | Ex. 19 | 2.33 | 353 | 56.6 | × | 86.0 | = 48.7 | 25.9 | 80.7 |
| 20 | Ex. 20 | 5.0 | 360 | 95.1 | × | 82.6 | = 78.6 | 24.6 | 63.9[a] |
| | | | 360 | 87.4 | × | 82.1 | = 71.9 | 21.6 | 66.7[b] |
| | | | 360 | 79.4 | × | 80.5 | = 63.9 | 20.1 | 63.6[c] |
| 21 | Ex. 21 | 5.0 | 361 | 98.9 | × | 48.9 | = 48.4 | 54.5 | 17.8[a] |
| | | | 360 | 86.2 | × | 81.8 | = 70.5 | 21.6 | 65.4[b] |
| | | | 361 | 81.9 | × | 78.4 | = 64.2 | 18.6 | 69.3[c] |
| 22 | Ex. 22 | 5.0 | 361 | 76.5 | × | 82.1 | = 62.8 | 19.4 | 64.6[a] |
| | | | 360 | 59.3 | × | 83.4 | = 49.5 | 15.2 | 65.2[b] |
| | | | 359 | 53.4 | × | 80.8 | = 43.2 | 14.2 | 60.7[c] |
| 23 | Ex. 22 | 5.0 | 361 | 90.0 | × | 82.7 | = 74.4 | 23.1 | 64.3[a] |
| | | 5.0 | 362 | 79.1 | × | 82.4 | = 65.2 | 19.3 | 67.3[b] |
| | | 5.0 | 361 | 71.4 | × | 80.9 | = 57.8 | 17.6 | 65.7[c] |
| 24 | Ex. 22 | 5.0 | 363 | 97.2 | × | 80.8 | = 78.5 | 24.6 | 63.7[a] |
| | | 5.0 | 360 | 92.3 | × | 82.0 | = 75.7 | 21.3 | 71.1[b] |
| | | 5.0 | 360 | 89.9 | × | 80.5 | = 70.8 | 20.9 | 67.6[c] |
| 25 | Ex. 22 | 5.0 | 361 | 97.7 | × | 80.8 | = 78.9 | 25.2 | 62.8[a] |
| | | 5.0 | 361 | 94.9 | × | 80.5 | = 76.4 | 22.9 | 66.8[b] |
| | | 5.0 | 361 | 92.7 | × | 80.5 | = 74.6 | 21.5 | 69.4[c] |
| 26 | Ex. 23 | 5.0 | 362 | 95.5 | × | 78.4 | = 74.9 | 24.7 | 60.5[a] |
| | | 5.0 | 360 | 89.0 | × | 77.6 | = 69.1 | 22.9 | 60.4[b] |
| | | 5.0 | 361 | 80.1 | × | 78.1 | = 62.6 | 21.2 | 59.0[c] |
| 27 | Ex. 16 | 2.33 | 355 | 81.8 | × | 84.2 | = 68.9 | 35.1 | 84.2 |

TABLE III-continued

| Run No. | Catalyst From | Ratio | Treated Catalyst Temp. °C. | Formaldehyde C | × | S | = | Yield | Acetic Acid C | S |
|---|---|---|---|---|---|---|---|---|---|---|
| 28 | Ex. 16 | 8.0 | 355 | 94.4 | × | 78.9 | = | 74.5 | 17.9 | 53.3 |

[a] 0 to 45 minutes
[b] 45 to 195 minutes
[c] 195 to 245 minutes
Run numbers 6, 7, 22, 23, 24 and 25 represent different charge sizes of the catalyst.
Run 6 160 cc charge of catalyst (Ex. 3)
Run 7 52 cc charge of catalyst (Ex. 5)
Run 22 20 cc charge of catalyst (Ex. 22)
Run 23 40 cc charge of catalyst (Ex. 22)
Run 24 110 cc charge of catalyst (Ex. 22)
Run 25 200 cc charge of catalyst (Ex. 22)

The following table shows the use of acetic anhydride in place of acetic acid.

TABLE IV

| Run No. | Catalyst | Ratio | Temp. °C. | Formaldehyde C | × | S | = | Yield | Acetic Anhydride C | S |
|---|---|---|---|---|---|---|---|---|---|---|
| 29 | Ex. 5 | 1.15 | 273 | 96.6 | × | 73.2 | = | 70.7 | 48.7 | 63.4 |
| 30 | Ex. 6 | 1.15 | 275 | 99.0 | × | 72.9 | = | 72.2 | 48.1 | 65.3 |
| 31 | Ex. 7 | 1.15 | 300 | 96.3 | × | 77.8 | = | 74.9 | 48.7 | 78.0 |

What is claimed is:

1. A supported catalyst of the formula:

$$(\text{Lewis Acid})(B_2O_3)_x(P_2O_5)_y(\text{Support})_z$$

wherein x is 0 to 1; y is 0 to 1; the sum of x plus y is 1 and Z is 0.5–999 which is prepared in the presence of a nitrogenous material which nitrogenous material is removed upon calcining at a temperature in the range of from 450° to about 600° C.

2. The catalyst of claim 1 wherein the support is selected from a silica, silica gel, titanium dioxide, alumina, a carbonaceous adsorbent, cordierite, zeolite, lanthanum oxide or combinations thereof.

3. The catalyst of claim 1 of the formula:

$$(\text{Lewis Acid})(B_2O_3)_x(P_2O_5)_y(\text{Silica gel})_z$$

wherein x is 0 to 1; y is 0 to 1; the sum of x plus y is 1 and Z is 0.5–999.

4. The catalyst of claim 1 wherein the Lewis acid is boron trifluoride.

5. The catalyst of claim 1 wherein the nitrogenous material is selected from urea, ammonium halide, hexamethylenetetramine, guanidine, ammonia, ammonium phosphate or lower ($C_1$–$C_5$) or di-lower alkyl amines.

6. The catalyst of claim 1 wherein the nitrogenous material is selected from ammonium chloride, urea, hexamethylenetetramine or guanidine, and the acidity enhancer is boron trifluoride.

7. The catalyst of claim 6 of the formula:

$$(BF_3)_a(B_2O_3)_x(P_2O_5)_y(\text{Silica gel})_z$$

wherein a is 0.1 to 1, x is 0 to 1, y is 0 to 1, x plus y is 1 and z is 0.5 to 999.

8. The catalyst of claim 7 where a is 0.49, x is 0.295, y is 0.705 and z is 9.

* * * * *